United States Patent [19]

Bursell et al.

[11] Patent Number: 4,836,207
[45] Date of Patent: Jun. 6, 1989

[54] METHOD AND APPARATUS TO MONITOR CHOLESTEROL LEVELS WITH PHOTON CORRELATION SPECTROSCOPY

[75] Inventors: Sven-Erik Bursell, Newton; Juan R. Serur, Newton Center, both of Mass.

[73] Assignee: The Beth Israel Hospital Association, Boston, Mass.

[21] Appl. No.: 95,052

[22] Filed: Sep. 9, 1987

[51] Int. Cl.[4] .............................................. A61B 10/00
[52] U.S. Cl. ..................................... 128/633; 128/665; 128/745
[58] Field of Search ............... 128/745, 633, 664, 665, 128/666

[56] References Cited

U.S. PATENT DOCUMENTS

| | | | |
|---|---|---|---|
| 3,963,019 | 6/1976 | Quandt | 128/633 |
| 4,350,163 | 9/1982 | Ford et al. | 128/745 |
| 4,702,576 | 10/1987 | Magnante | 128/745 |

OTHER PUBLICATIONS

Kelly et al., Bailen's Textbook of Microscopic Anatomy, Eighteenth Ed., Williams and Wilkens, Baltimore/London, 1984, pp. 835-841.
Scientific Tables, 7th Ed., edited by Diem et al., Ciba—Geigy Ltd., Basle, Switzerland, 1970, p. 602.
S. Grundy, The Effects of Diet on Plasma Cholesterol
M. Winston, Measurements and Patterns of Food Consumption.
R. Levy, Cholesterol Screening—When, Why, and How?.
P. Bachorik, Improved Approaches to the Laboratory.

"Cholesterol Levels Assessed with Photon Correlation Spectroscopy", *SPIE*, vol. 712, Lasers in Medicine (9/14/86), by Bursell et al.

*Primary Examiner*—Francis Jaworski
*Assistant Examiner*—John C. Hanley
*Attorney, Agent, or Firm*—Lorusso & Loud

[57] ABSTRACT

A method to determine the cholesterol level in a patient in a non-invasive manner by delivering a beam of light to a patient's eye. The intensity of light scattered from the aqueous of the eye and the mobility of the protein scatterers in the eye are measured and compared to a control.

An apparatus to detect the cholesterol level in a patient in a non-invasive manner which delivers a beam of light to a patient's eye, collects the scattered light from the patient's eye and correlates the scattered light to a cholesterol level measurement.

2 Claims, 3 Drawing Sheets

METHOD AND APPARATUS TO MONITOR CHOLESTEROL LEVELS WITH PHOTON CORRELATION SPECTROSCOPY

BACKGROUND OF THE INVENTION

This invention relates to a method and apparatus to monitor, detect and determine cholesterol levels and more particularly, it relates to a method to monitor high cholesterol levels in a non-invasive manner with photon correlation spectroscopy.

Cholesterol is a steroid alcohol and is present in animal cells and body fluids. It is known that high levels of cholesterol of the blood lead to a build up of plaque on the wall of arteries and veins thereby restricting blood flow and causing a dangerous health situation. The condition of an excessive amount of plaque build up in the arteries and veins is known as atherosclerosis. Build up of excessive amount of plaque in the arteries is called artereosclerosis.

There is a school of thought which indicates that high cholesterol levels in the blood are caused by a person's diet. Those foods which have a significant cholesterol content are meat, poultry, fish, eggs, dairy products (including cheese, cream, milk and yogurt), fats and oils (including butter, lard, shortening, margarine, mayonnaise, peanut butter, palm oil, coconut oil and soybean oil). See Winston, M., A. Owen, Measurement and patterns of food consumption in the U.S., Cholesterol and Coronary Disease . . . Reducing the Risk, 1:5 (1987). Diet is also responsible for raising low-density lipoprotein (LDL) levels and can contribute to hypercholesterolemia. See Grundy, S.M., The effects of diet on plasma cholesterol, Cholesterol and Coronary Disease . . . Reducing the Risk, 1:1 (1987). Most LDL is derived from the catabolism of very low-density lipoproteins (VLDL) which are secreted by the liver. Saturated fatty acids, which are found in animal and plant fats, generally raise the plasma LDL level. The most potent cholesterol raising fats are coconut oil, butter fat and palm oil. Meat fats, such as beef, pork and chicken, and cocoa butter, the fat in chocolate, raise the plasma cholesterol level approximately half as much as palm oil.

Early detection of an abnormally high cholesterol level is important in order to prevent the more serious problems associated with artereosclerosis. Early detection is important because if detected early, proper diet can be prescribed by a physician which will prevent the build up of the condition which leads to atherosclerosis.

A significant drawback with monitoring or measuring cholesterol levels from blood samples is that this technique obviously requires the withdrawal of blood from a patient. It also requires a significant amount of time for the blood to be analyzed and the results returned to the physician for diagnosis and prescription of a proper diet.

SUMMARY OF THE INVENTION

In accordance with the present invention, it has been discovered that light scattering characteristics of both the lens and the aqueous of a human eye change in relation to the cholesterol level in a patient. Furthermore, equipment presently exists which with modification is capable of measuring these light scattering characteristics and correlating those measurements into a cholesterol level reading.

Accordingly, the present invention is a non-invasive technique to monitor the level of blood cholesterol in a patient by measuring light scattering characteristics of the anterior chamber of the eye. A reading is taken from the aqueous using the technique of quasi-elastic light spectroscopy. Any increase in the level of cholesterol is observed by a marked increase in scattering of the aqueous as analyzed from these readings. In this manner, early detection of an elevated blood cholesterol level can be made, and appropriate steps can be observed to decrease that level.

It is therefore an object of the present invention to provide a method to monitor the levels of cholesterol in a patient.

It is another object of the present invention to provide a method to detect and/or determine and/or monitor the levels of cholesterol in a patient in a non-invasive manner.

It is a further object of the present invention to provide a method to detect and monitor the presence and level of cholesterol in a patient in a non-invasive manner by examination of the aqueous or anterior chamber of the eye to detect any subtle changes in light scattering characteristics of the aqueous.

DESCRIPTION OF THE PREFERRED EMBODIMENTS

At the outset, the invention is described in its broadest overall aspects with a more detailed description following. The broadest aspects of the invention involve passing a beam of light through the anterior chamber of the patient's eye and measuring the light scattering characteristics from the lens and correlating those light scattering characteristics to determine a patient's cholesterol level. The technique is non-invasive and safe as light levels are low and will not be directly incident on the retina. Furthermore, the results are immediately obtainable by a physician.

The subject's eye will be at no risk during this procedure as the light level from the laser is low (1.5 mW). a short working distance lens causes the beam of light to rapidly diverge beyond the focal point so that overall illuminance posterior to the focal point is low. In addition, even if the beam from the laser was directly incident on the retina, this beam would have to be stationalry on the retina for over one (1) hour before there was any risk of harm to the retina. The measurement itself is performed in 5 seconds. It is highly unlikely that this beam will be incident on the retina as the pupil will not be dilated and this light beam will travel across the aqueous from the temporal to the nasal side. Thus the light beam will travel across the pupil of the eye rather than through it.

The present invention builds on a prior discovery that diabetes can be diagnosed by measuring the light scattering characteristics of the lens. A brief discussion of this procedure follows.

In simplest terms it is known that the disease diabetes causes a condition in which the lens becomes less transparent; thus, a measurement of the opacification of the lens can be correlated to determine the diabetic condition.

Recently, researchers have used a method of photon correlation spectroscopy or quasi-elastic light scattering spectroscopy to provide a non-invasive probe of the development of lens opacities associated with diabetes.

Figure 1:
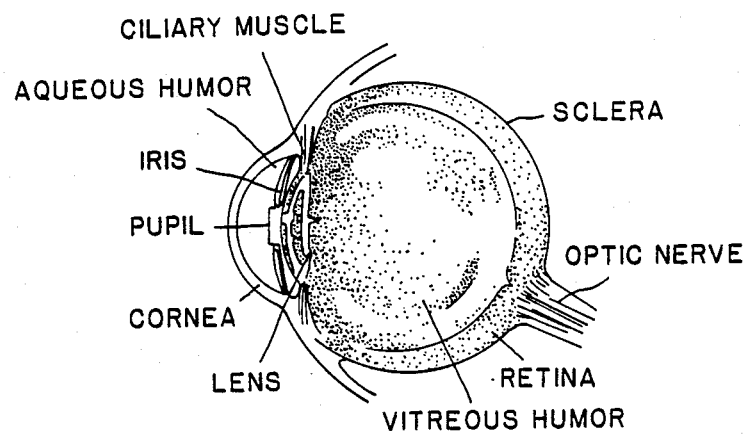
FIG. 1 is a diagram of an eye showing the aqueous (labeled as aqueous humor) and the lens.

The lens of the eye is an encapsulated, avascular, continually-growing organ in the anterior of the eye. For purposes of this specification and claims, the term aqueous is intended to describe the aqueous humor of the eye. As shown in FIG. 1, the aqueous humor is anterior to the lens of the eye. It is a transparent, watery fluid that is continually being replaced. The vitreous humor is a similar fluid which is posterior to the lens and gives the eye its shape.

The maintenance of lens transparency is essential for normal vision. Traditional techniques for assessing lens transparency rely on slit lamp observation. This is not an acceptable index as a lens region can appear perfectly clear on slit lamp examination, yet may exhibit significant cellular abnormalities.

Lens transparency depends on the spatial ordering of lens proteins in the lens fiber cells. Thus, any localized alteration in the density and/or structural integrity of this ordering due to aggregation, conformational changes, or changes in lens hydration can result in regional changes in refractive index and lens transparency leading to the development of opacities. The prevention or reversal of the development of opacities or cataracts therefore requires a sensitive method of in vivo detection, at the molecular level, of the subtle lens changes that initiate the opacification process.

Conventional techniques for examination of the eye do not provide such a method. Scheimpflug photography, a non-invasive technique for the detection of lens changes, provides quantitation of the optical density changes arising from opacification in the lens. Cataractic changes measured by this technique do not, however, explain the primary causes of opacification such as changes in lens protein conformation. Laser Raman spectroscopy offers the potential of quantitating some of these early lens changes such as the quantitation of sulfhydryl and disulfide bond formation implicated in the lens protein aggregation process. This method is currently restricted to in vitro measurement.

With modifications in accordance with the present invention, equipment and techniques used in the past to measure the opacity of a lens can be used to measure the scattering of light through the aqueous. The changes in the levels of cholesterol in the blood affect the scattering of light as it passes through the aqueous. These changes can be accurately quantitated. At the outset, it should be noted, that it is not readily clear whether this light scattering is due to the presence of the ingested cholesterol molecule itself or whether it is the result of some other metabolic activity taking place in the body which manifests itself by increased light scattering in the aqueous and in the lens of the eye. At this point, it should be noted that no correlation has ever been made between high cholesterol and vision, therefore it was an unexpected discovery that high cholesterol would manifest itself as changes in the scattering properties of the aqueous.

Figure 2:
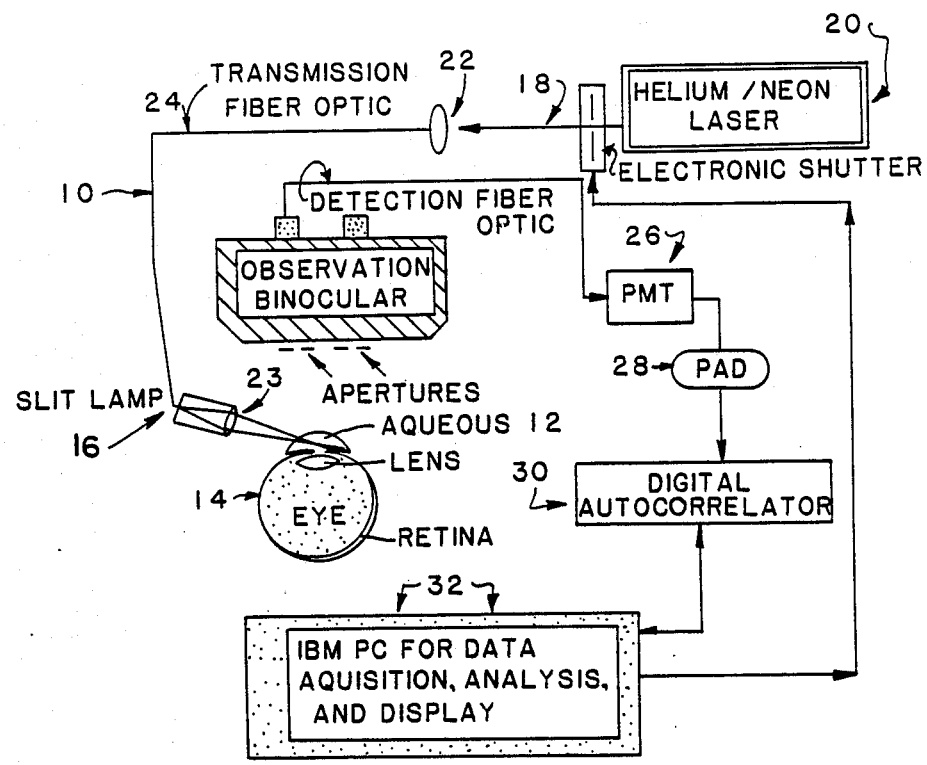
FIG. 2 is a schematic diagram of the quasi-elastic light spectroscopy instrumentation used in the method of the present invention.

The instrumentation used in the method of the present invention is as follows and is illustrated in FIG. 2. The quasi-elastic light spectroscopy apparatus 10 is based on a modified Haag-Striet slit lamp biomicroscope which is used to deliver the incident illumination to a focus in aqueous of the eye 14 and to collect the resulting scattered intensity. The incident illumination is provided by a 5 mW Helium/Neon laser (632.8 nm wavelength light) 20. Beam 18 from laser 20 is passed through an attenuator to reduce the laser beam power and is focused onto a 100 $\mu$m core optical fiber 24 using a 40 x microscope objective lens 22. The optical fiber 24 delivers the illumination light to the slit lamp 16. The output beam from this fiber is brought to a 37 $\mu$m diameter focal spot in the lens of the eye using a short-working distance lens 23. The power incident on the cornea is 1.5 mW. The illumination optics are mounted on the slit lamp using a third arm designed to attach to the central rotation axis of the slit lamp. This arm fixes the scattering angle between illumination and observation light paths at 130%. Micrometers attached to the arm allow adjustments in the vertical and axial directions in addition to rotation about the vertical axis. These adjustments ensure that the laser light illumination is parfocal with the regular slit lamp illumination and observation optics. Divergence of the rapid beam from the focal plane ensures low retinal illuminance, approximately 20 mW/cm$^2$, giving a maximum permissable retinal exposure time of 1000 seconds.

The optical section of the laser beam in the aqueous is viewed through the standard binocular observation eyepiece of the slit lamp. A 150 $\mu$m diameter optical fiber is positioned at the image plane in one of the observation oculars and centered over the image of the focal spot in the aqueous. Vertical micrometer adjustments of the incident laser beams facilitates the centering of the image of the focal spot of the beam in the aqueous of the eye over the collecting fiber optic in the eyepiece. The light backscattered from the focal spot in the aqueous is collected through this fiber optic. This optical geometry restricts the measurements to one coherence area in the aqueous 12. An aperture positioned in front of the input to the observation optics limits the collection angle for the scattered light and discriminates against light scattered from regions other than the measurement site. The collection fiber optic is coupled to a fiber optic bundle mounted in the eyepiece which delivers the back scattered light to a photomultiplier for detection and processing.

A photon counting photomultiplier (PMT) 26 detects the scattered light signals and the resulting photocurrent pulses are processed through a pre-amplifier discriminator (PAD) 28 to provide a digital photopulse output. This digital signal is processed using a 128 channel digital autocorrelator 30. The resulting intensity autocorrelation function is stored and analyzed. The IBM PC computer 32 controls the measurement acquisition process and stores the results. The system was calibrated routinely using solutions of microspheres of known size.

The light scattered from the aqueous is analyzed in the form of an intensity autocorrelation function using the methodology of quasi-elastic light scattering spectroscopy. This technique measures the temporal fluctuations and scattered light intensity resulting from Brownian motion of the aqueous protein scattering elements. The temporal fluctuations and scattered light intensity are proportional to the photocurrent fluctuation output of the photomultiplier and is analyzed using a 128 channel digital autocorrelator. The autocorrelator provides an intensity autocorrelation function of these fluctuations in the form:

$$g(T) = \langle i(t)i(t+T) \rangle$$

For T varying from $\Delta T$ to $128 \times \Delta T$ where $\Delta T$ the sample time can be chosen from 100 ns to 1 s.

In the simplest case of light being scattered from a single scattering species undergoing translational Brownian motion, the resulting autocorrelation functions will have the form:

$$g(T) = i^2(1 + exp(-2T/T_1))$$

Where $T_1$ is the characteristic decay time and i is the scattered light intensity detected by the PMT. The decay constant $\Gamma = 1/T_1$ is related to the diffusion coefficient, D, of the scatterers by $$\Gamma = Dq^2$$

where $q = (4\pi/\lambda) \sin \theta/2$ and $\theta$ is the scattering angle. $\lambda$ is the wavelength light (632.8 nm). The diffusion coefficient of the scatterers is related to their hydrodynamic radius (r) by the Stokes-Einstein relation, assuming that the scatterers are non-interacting, where $$D = K_B T_A / 6\pi\eta r$$

Where $K_B$ is Boltzman's constant, $T_A$ is the absolute temperature in degrees K, and $\eta$ is the viscosity of the medium.

In the lens of the eye, the autocorrelation function reflects a polydispersed sized distribution of protein. The decay of the autocorrelation function can no longer be described by a single exponential function. The method of cumulant analysis has been used to analyze these autocorrelation functions. A second order function was fit to the measured function. Higher order terms provide no useful information as the errors associated with the fitted parameters were large. The form of the function fit to the data is given by $$a(T) = -2\bar{\Gamma}T + \{(\Gamma - \bar{\Gamma})^2\}T^2$$

where a(T) is the natural logarithm of the normalized intensity autocorrelation function. The coefficient of the second order term denotes an average over a distribution of decay times. The degree of polydispersity of "Quality" (Q) is given by $$Q = \{(\Gamma - \bar{\Gamma})^2\}\bar{\Gamma}^2]^{\frac{1}{2}}$$

which is the ratio of the half width at half height to the average value of the distribution. For a monodispersed distribution of scatterers, the value of Q will equal zero.

Animal trials using rabbits illustrate correlations existing over a broad range of sample times. Measurements were made at different sample times. The results show that the value of Q exhibited local minima at sample times of $5\mu s$ and $100\mu s$. This indicated that at these sample times, the scattered signal contributing to the measured autocorrelation function was more nearly monoexponential in nature suggesting that, at these sample times, the scattered signal came from a predominantly well-defined size distribution of lens protein. Thus, the measurements at the $5\mu s$ and $100\mu s$ sample times allowed the quantification of two distinct sizes of lens protein scatterers. The measurements at the $5\mu s$ sample time were characteristic of smaller, more mobile lens proteins, while at the $100\mu s$ sample time were characteristic of slower moving, larger lens proteins.

Three sets of age matched albino New Zealand rabbits were used in this study. A set of three normal rabbits were measured at different times over the course of a year. A second set of four rabbits were used to investigate both chronic and acute effects of a high cholesterol diet. To investigate the acute effects of the diet, measurements were made everyday for five days after the start of the diet. The third set of four rabbits were used to provide additional data for the investigation of the chronic effects of the cholesterol diet on the lens of the eye. Blood samples were taken when possible, prior to the quasi-elastic light spectroscopy (QLS) measurement, to determine levels of total cholesterol in the blood.

Prior to the measurements, each rabbit eye was dilated using a drop of topically administered 1% Mydriacyl. The unanesthetized rabbit was then comfortably positioned on a specially designed device which left the eyes accessible for the QLS measurement. During the measurements, a drop of tear substitute was applied to prevent dehydration of the eye. The animals were maintained in accordance with the guidelines of the Committee on Animals of the Harvard Medical School. Measurements were made from the center of the lens nucleus on the optical axis of the lens. Four measurements were made at each sample time. The duration of each measurement was 5 seconds. The corresponding decay constants, determined using cumulant analysis, were averaged to provide a mean decay constant for each rabbit lens at each sample time. The effects of eye movements in the course of a measurement have been shown to have little effect on the measurements. However, at the longer sample time used here, eye movements tended to increase the variance in the calculated average decay constant.

Measurements were made from the three normal rabbits to assess the reproducibility of the measurements from the lens. The measurement sessions were separated in time by two hours. The results are presented in Table 1 for the average decay constants obtained at each sample time at the constants obtained at each sample time at the two different measurement times. There were no statistically significant differences between the two reading at each sample time for each rabbit.

TABLE 1

| | REPRODUCIBILITY | |
|---|---|---|
| RABBIT | AVERAGE DECAY AT 5 $\mu$S ST ($\pm$ SD) (S$^{-1}$) | AVERAGE DECAY AT 100 $\mu$S ST ($\pm$ SD) (S$^{-1}$) |
| J 25 | 183 $\pm$ 45 | 82 $\pm$ 19 |
| J 25 (2 HOURS LATER) | 192 $\pm$ 39 | 96 $\pm$ 13 |
| J 26 | 160 $\pm$ 39 | 90 $\pm$ 19 |

TABLE 1-continued

| RABBIT | REPRODUCIBILITY AVERAGE DECAY AT 5 μS ST (± SD) (S$^{-1}$) | AVERAGE DECAY AT 100 μS ST (± SD) (S$^{-1}$) |
|---|---|---|
| J 26 (2 HOURS LATER) | 191 ± 48 | 90 ± 27 |
| J 27 | 156 ± 46 | 128 ± 18 |
| J 27 (2 HOURS LATER) | 164 ± 43 | 101 ± 24 |

Figure 3:
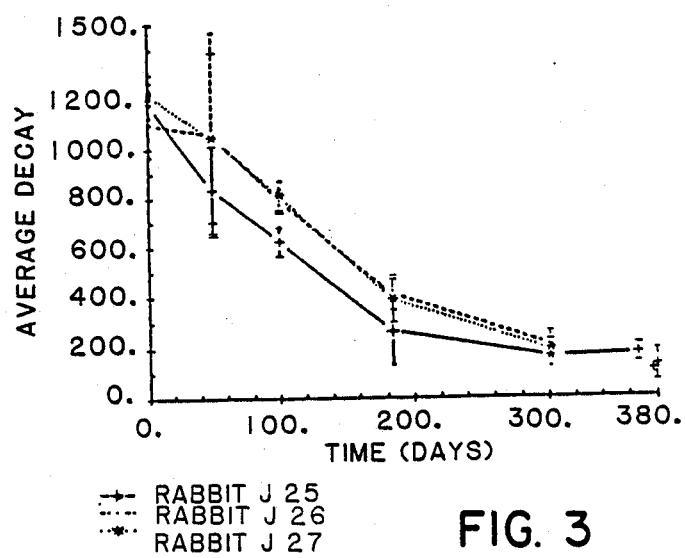
FIG. 3 illustrates the average decay constant obtained using the method of the present invention from normal rabbits over a period of 380 days at the 5 microsecond ($\mu$s) sample time.
Figure 4:
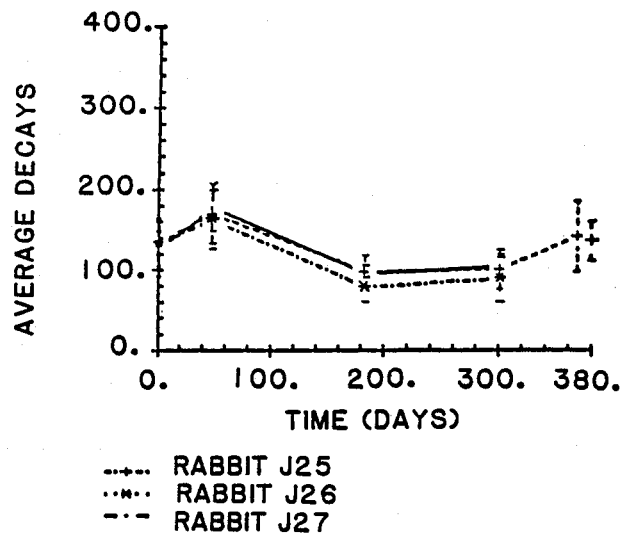
FIG. 4 illustrates the average decay constant obtained using the method of the present invention from normal rabbits over a period of 380 days at the 100 $\mu$s sample time.

FIGS. 3 and 4 illustrate the average decay constant obtained from the normal rabbits over a period of 380 days at the 5μs and 100μs sample times, respectively. The results in the 5μs sample time demonstrates the significant decrease in the decay constant or diffusion coefficient with increasing age of the rabbit. There were no marked changes in the decay constants measured at the 100μs sample time over the same period. On comparing the two sets of results, it can be noted that the decay constants at the 5μs sample times became comparable to those determined at the 100μs sample time in the older rabbits. This would indicate that, at these later times, most of the population of smaller protein scatterers had undergone aggregation to form larger protein molecules characteristic of those measured at the 100μs sample time.

The chronic effects of a high cholesterol diet on the lens of the eye were investigated by comparing the group of normal rabbits with an age-matched group of rabbits at a high cholesterol diet after 100 days. In this case, the rabbits on the high cholesterol diet had been on the diet for 94 days. The results at the 5μs sample time are presented in Table 2.

TABLE 2

COMPARISON BETWEEN NORMAL AND AGE MATCHED CHOLESTEROLEMIC RABBITS AT 100 DAYS

| | AVERAGE DECAYS (S$^{-1}$) AT 5 μS SAMPLE TIME | |
|---|---|---|
| NORMAL GROUP | | |
| J25 | 624 ± 59 | |
| J26 | 790 ± 48 | |
| J27 | 810 ± 63 | |
| | | AVERAGE DECAY = 741.3 ± 102.1 s$^{-1}$ |
| CHOLESTEROLEMIC GROUP | | |
| K1 | 268 ± 55 | |
| L6 | 202 ± 58 | |
| L7 | 149 ± 56 | |
| L8 | 249 ± 52 | |
| L10 | 299 ± 63 | |
| | | AVERAGE DECAY = 233.4 ± 58.4 s$^{-1}$ |

There was a statistically significant difference in lens decay constants between the normal and cholesterol-fed groups. The decay constants of the cholesterol-fed group were approximately 3 times lower than those from the normal group. There was no statistically significant difference between the two groups at the 100μs sample time.

Figure 5:
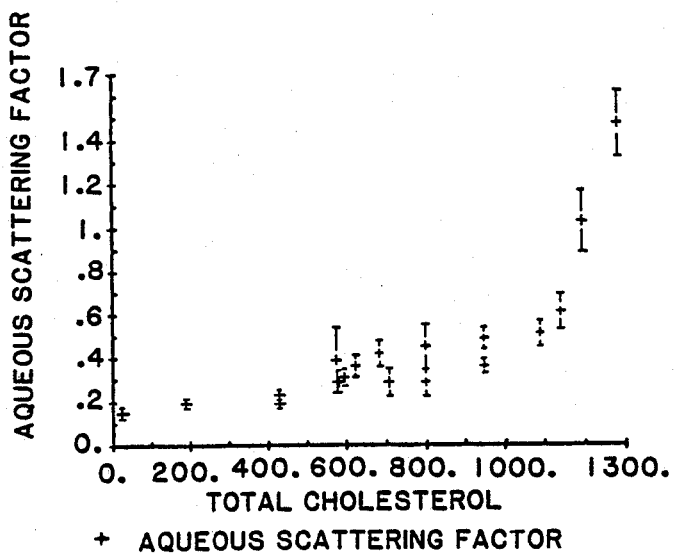
FIG. 5 is a standard curve showing the dependence of the aqueous scattering factor on the total blood cholesterol level in the method of the present invention.

It was noted, while performing measurements on the lenses of the cholesterol fed rabbits, that the aqueous became quite highly scattering. It was decided to perform QLS measurements from the aqueous of the normal and cholesterolemic rabbits. The scattered intensity from the aqueous was measured from 13 rabbits on cholesterol diets. Blood cholesterol levels were determined from blood levels drawn before the measurements. The scattered light intensity from the aqueous was normalized with respect to the measured scattered intensity from the lens to provide an "aqueous scattering factor". FIG. 5 demonstrates the dependence of this factor on the total blood cholesterol level. As the cholesterol levels increase, we note a slow increase in the aqueous scattering factor. At the higher cholesterol level, the scattered intensity from the aqueous increases very rapidly and becomes greater than that from the lens. In addition, autocorrelation functions were measured from the aqueous once the aqueous scattering became more prominent. Autocorrelation functions measured at different sample times, show that the scattered signal originated from a fairly monodispersed distribution of scatterers. Based on cumulant analysis, a sample time of 5μs was chosen as optimum for characterizing the decay constant of these scatterers. Two different decay constants were measured depending on the relative magnitude of the scattered intensity from the aqueous. For the more intensely scattering aqueous the average decay constant determined from 7 rabbits measured at 18 different times was 7390±462 s$^{-1}$. The corresponding diffusion coefficient was $1.14+0.07\times10^{-7}$ cm$^2$/s and the resulting hydrodynamic radius was calculated to be 190±12 Å assuming that the aqueous had a viscosity equal to that of water. For the less intensely scattering aqueous the average decay constant obtained from 7 rabbits measured at 12 different times was 4268±882 s$^{-1}$. The diffusion coefficient and hydrodynamic radius of these scatterers was calculated to be $6.59\pm1.36\times10^{-8}$ cm$^2$/s and 330 +68 Å respectively.

The measurements made from the aqueous show that scattering contributions arise from two different species. The average hydrodynamic radii of 190 Å and 330 Å suggest that the scattering results from different types of lipoproteins which are known to have sizes in the range between 200 and 400 Å. The reduction in back-scattered intensity from the larger particles is possibly a consequence of a more efficient forward scattering in the case of the larger particles.

The results on the effects of high cholesterol on the rabbit eye indicate that QLS measurements can provide a useful, non-invasive method for quantitating systemic cholesterol effects. The measurements from the aqueous may provide a useful, clinical method for the non-invasive monitoring of blood cholesterol levels.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and there is no intention to exclude any equivalence thereof. Hence, it is recognized that various modifications are possible and within the scope of the present invention as claimed.

What is claimed is:

1. Apparatus for monitoring serum cholesterol levels in a non-invasive manner comprising:
   (a) a slit lamp biomicroscope including an illumination optical system comprising a laser beam, an attenuator for reducing the power of said laser beam, and a microscope objective lens for focusing said laser beam onto an optical fiber for delivering said laser beam to said slit lamp biomicroscope;
   (b) illumination optics mounted on said slit lamp biomicroscope such that light from said laser beam is backscattered from a focal point in the aqueous of a patient's eye and collected through a collecting fiber optic at an approximately 130% angle with said laser beam;
   (c) a photon counting photomultiplier (PMT) for detecting said backscattered light;
   (d) a preamplifier discriminator for converting said backscattered light from said PMT to a digital photopulse output;
   (e) a digital autocorrelator for measuring temporal time dependent fluctuations and scattered light intensity in said digital photopulse output;
   (f) a means for normalizing scattered light intensity from the aqueous with respect to scattered intensity measured from the lens of a patient's eye and means for correlating said normalized scattered light intensity measurement to a serum cholesterol level wherein a patient's serum cholesterol level is measured b correlating a normalized scattered light intensity from the aqueous of the patient's eye to a serum cholesterol level.

2. A method for monitoring serum cholesterol levels in a non-invasive manner comprising the steps of:
   (a) directing a low power laser beam to the aqueous of a patient's eye for scattering by molecules in the aqueous of the patient's eye;
   (b) receiving a backscattered laser light from the aqueous and converting the backscattered light into an electrical signal;
   (c) measuring time dependent fluctuations of said signal and calculating the autocorrelation function associated with said fluctuations;
   (d) converting said autocorrelation function to a two-component exponential decay curve;
   (e) computing the amplitudes and fluctuation rates of said two components; and
   (f) utilizing said amplitudes and fluctuation rates of said two components by relating them to two species of protein in said aqueous whereby the relative degree of laser light scattering by said two protein species in a patient's aqueous can be normalized with respect to laser light scattered in a patient's lens and correlated to a serum cholesterol level.

* * * * *